US012121230B2

(12) United States Patent
Bechtold et al.

(10) Patent No.: US 12,121,230 B2
(45) Date of Patent: Oct. 22, 2024

(54) FORCE MEASURING JOINT DISTRACTION LEVER

(71) Applicant: MAKO Surgical Corp., Weston, FL (US)

(72) Inventors: Kevin Bechtold, Weston, FL (US); Jason Otto, Plantation, FL (US); Hyosig Kang, Weston, FL (US); Radu Iorgulescu, Weston, FL (US)

(73) Assignee: MAKO Surgical Corp., Weston, FL (US)

( * ) Notice: Subject to any disclaimer, the term of this patent is extended or adjusted under 35 U.S.C. 154(b) by 0 days.

(21) Appl. No.: 18/137,546

(22) Filed: Apr. 21, 2023

(65) Prior Publication Data

US 2023/0248349 A1     Aug. 10, 2023

Related U.S. Application Data

(60) Continuation of application No. 17/132,053, filed on Dec. 23, 2020, now Pat. No. 11,660,083, which is a
(Continued)

(51) Int. Cl.
*A61B 17/02* (2006.01)
*A61B 17/16* (2006.01)
(Continued)

(52) U.S. Cl.
CPC ............ *A61B 17/025* (2013.01); *A61B 17/16* (2013.01); *A61B 17/1675* (2013.01);
(Continued)

(58) Field of Classification Search
CPC .......... A61B 17/025; A61B 2017/0268; A61B 34/10; A61B 34/20; A61B 34/70; A61B 34/30
See application file for complete search history.

(56) References Cited

U.S. PATENT DOCUMENTS

| 4,995,875 A | 2/1991 | Coes |
| 5,431,653 A | 7/1995 | Callaway |

(Continued)

FOREIGN PATENT DOCUMENTS

| DE | 20 2010 000 341 U1 | 5/2010 |
| EP | 2 011 442 A1 | 1/2009 |
| GB | 2 455 182 | 6/2009 |

OTHER PUBLICATIONS

International Search Report and Written Opinion for International Application No. PCT/US2015/032973, mailed Sep. 24, 2015, 14 pages.

*Primary Examiner* — Samuel S Hanna
(74) *Attorney, Agent, or Firm* — FOLEY & LARDNER LLP

(57) ABSTRACT

A joint distraction lever, comprising a lever body comprising a handle portion and a working portion, a distal tip coupled to the working portion, and a fulcrum extending from a bottom surface of the working portion and spaced apart from the distal tip such that the fulcrum is positioned between the distal tip and the handle portion, where the joint distraction lever is configured to determine a distraction force based on deformation of the joint distraction lever.

20 Claims, 9 Drawing Sheets

Related U.S. Application Data division of application No. 14/724,381, filed on May 28, 2015, now Pat. No. 10,918,368.

(60) Provisional application No. 62/004,015, filed on May 28, 2014.

(51) Int. Cl.
    *A61B 34/20*     (2016.01)
    *A61B 17/00*     (2006.01)
    *A61B 90/00*     (2016.01)

(52) U.S. Cl.
    CPC ............... *A61B 2017/00115* (2013.01); *A61B 2017/0268* (2013.01); *A61B 34/20* (2016.02); *A61B 2090/064* (2016.02)

(56) References Cited

U.S. PATENT DOCUMENTS

| | | | |
|---|---|---|---|
| 6,558,392 | B1 | 5/2003 | Martini |
| 6,859,661 | B2 | 2/2005 | Tuke |
| 8,010,180 | B2 | 8/2011 | Quaid et al. |
| 8,162,951 | B2 | 4/2012 | Kaufman |
| 8,211,041 | B2 | 7/2012 | Fisher et al. |
| 8,516,907 | B2 | 8/2013 | Stein et al. |
| 9,351,850 | B2 | 5/2016 | Fischer et al. |
| 2009/0198240 | A1 | 8/2009 | Kaufman |
| 2010/0198275 | A1 | 8/2010 | Chana et al. |
| 2010/0217156 | A1 | 8/2010 | Fisher et al. |
| 2010/0249658 | A1 | 9/2010 | Sherman et al. |
| 2010/0250571 | A1 | 9/2010 | Pierce et al. |
| 2010/0326210 | A1 | 12/2010 | Stein et al. |
| 2010/0331737 | A1 | 12/2010 | Stein et al. |
| 2011/0319755 | A1 | 12/2011 | Stein et al. |
| 2012/0232429 | A1 | 9/2012 | Fischer et al. |
| 2012/0330368 | A1 | 12/2012 | Dunn |
| 2013/0023795 | A1 | 1/2013 | Stein et al. |
| 2013/0079669 | A1 | 3/2013 | Stein et al. |
| 2013/0079670 | A1 | 3/2013 | Stein et al. |
| 2013/0079674 | A1 | 3/2013 | Stein et al. |
| 2013/0079675 | A1 | 3/2013 | Stein et al. |
| 2013/0079792 | A1* | 3/2013 | Stein ............ A61F 2/4611 606/102 |
| 2013/0079884 | A1 | 3/2013 | Stein et al. |
| 2013/0102929 | A1 | 4/2013 | Haight et al. |
| 2013/0103038 | A1 | 4/2013 | Fischer et al. |
| 2013/0226036 | A1 | 8/2013 | Stein et al. |
| 2015/0342588 | A1 | 12/2015 | Bechtold et al. |
| 2018/0008138 | A1 | 1/2018 | Thommen et al. |

\* cited by examiner

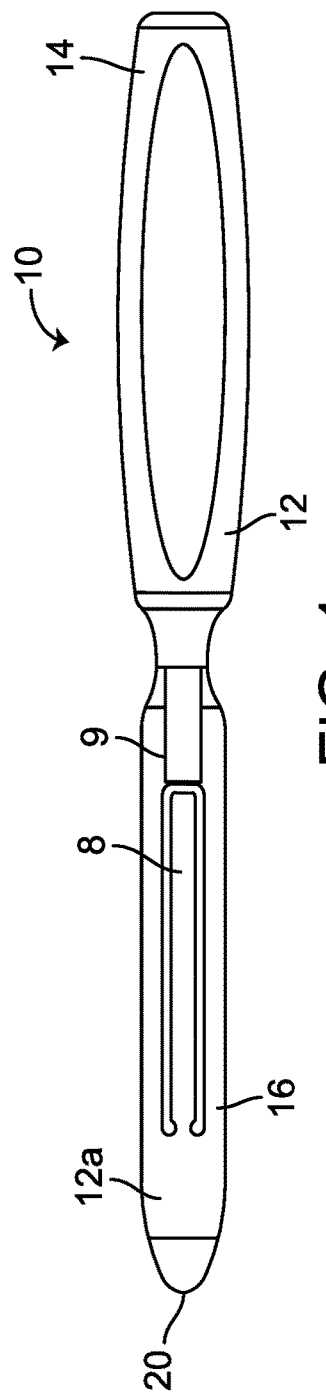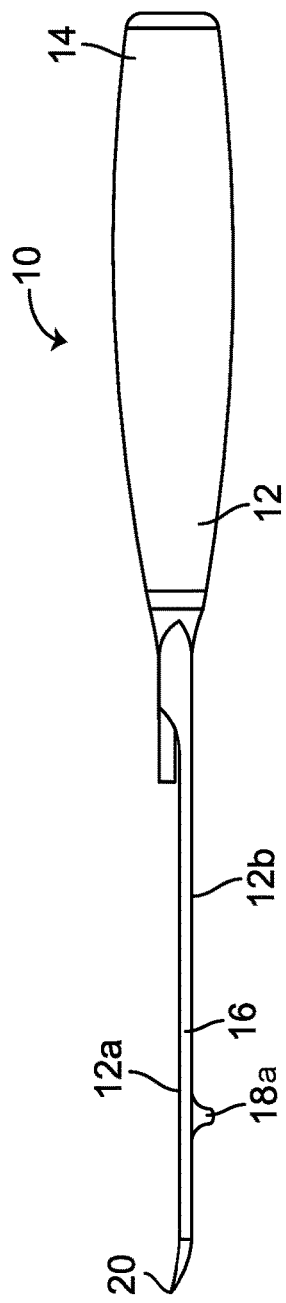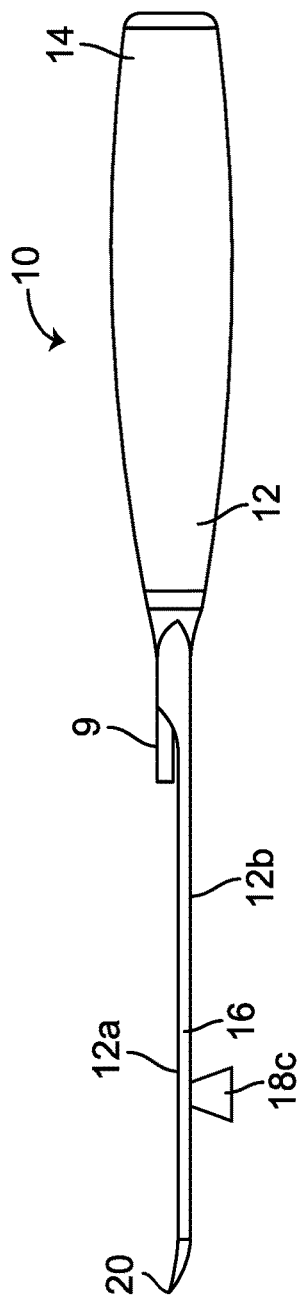
FIG. 1
FIG. 2A
FIG. 2B

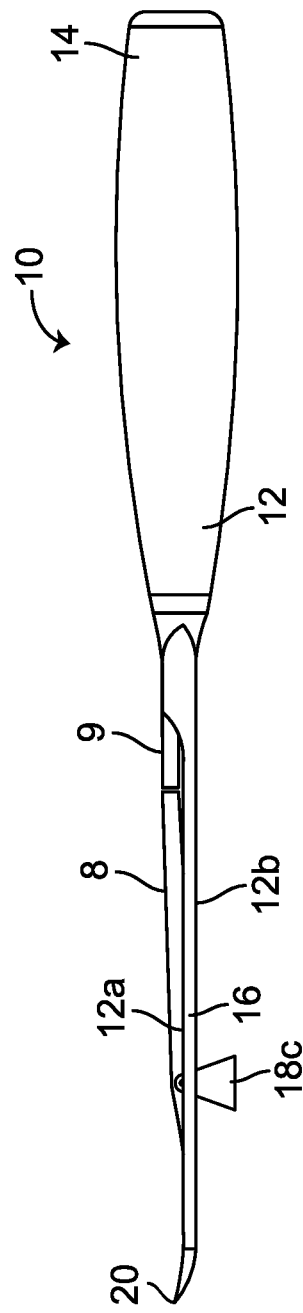
FIG. 2C
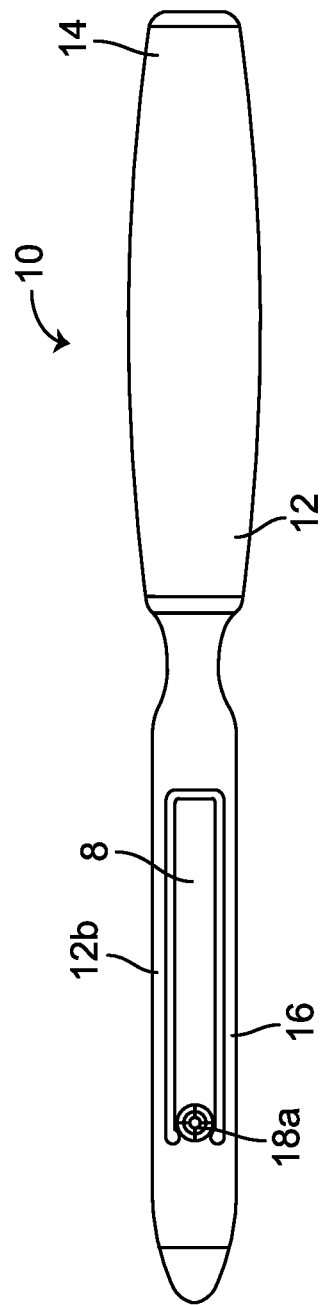
FIG. 3A
FIG. 3C
FIG. 3B

FORCE MEASURING JOINT DISTRACTION LEVER

CROSS-REFERENCE TO RELATED APPLICATIONS

The present application is a continuation of U.S. patent application Ser. No. 17/132,053, filed Dec. 23, 2020, which is a divisional of U.S. patent application Ser. No. 14/724,381, filed May 28, 2015, now U.S. Pat. No. 10,918,368, which claims the benefit of and priority to U.S. Provisional Patent Application No. 62/004,015, filed May 28, 2014 and titled "Force Measuring Joint Distraction Lever," the entireties of which are incorporated by reference herein.

BACKGROUND

The present invention relates generally to the field of surgical tools for use during planning and preparation of a joint replacement procedure, and more particularly to a force measuring lever for use during joint distraction.

Over time, as a result of disease, injury, or longevity of use, bones of a joint may degenerate, resulting in pain and diminished functionality. To reduce pain and restore functionality, a joint replacement procedure may be necessary. Examples of such procedures may be total or partial knee arthroplasty, total hip arthroplasty, or knee or hip resurfacing. In these procedures, portions of a patient's joint are replaced with artificial components. Particularly, a surgeon uses a surgical cutting tool to remove portions of bone to prepare the bone to receive a prosthetic device. Prior to resection of the bone, the surgeon plans bone preparation specific to the patient's anatomy, size, current state of the target joint, and several other factors in order to determine the portions of the bone that will be removed and replaced by one or more prosthetic components, as well as to determine proper positioning of the one or more prosthetic components.

One step of surgical planning for a partial knee resurfacing procedure involves a knee joint distraction, that is, forced separation of the distal femur from the proximal tibia. For partial knee resurfacing, this is intended to correct knee joint deformity and cause proper re-tensioning of the ligaments of the knee to determine a desired, post-procedure joint construction. In one exemplary method, prior to resection and prior to a creating a final implant plan, the knee joint deformity is corrected at multiple flexion positions or flexion angles by distracting the joint. An instantaneous six degree-of-freedom (DOF) position (i.e. the pose) of the femur with respect to the six DOF position of the tibia is captured at each of the multiple flexion positions. For example, a common flexion position is near full extension where the surgeon applies a *valgus* torque to the tibia when the leg is at approximately 5-10 degrees of flexion. The *valgus* torque corrects the limb alignment deformity and returns the ligaments to a proper tension state. Another common flexion position is 90 degrees flexion. With these two poses, the knee joint is in the desired post-resection final position. After collection of poses, bone resection, implant positioning, and implant characteristics are planned so as to maintain this relative alignment by making the femoral and tibial components contact (or be slightly gapped to allow for some laxity). Once the bone is resected at this desired plan and the trials and/or implants are secured to the bone, the leg will then be in the pre-resected posed positions.

A first technique currently used to apply a joint distraction force includes manually applying a *valgus* torque (for a *varus* knee) to the tibia portion of a patient's leg to pivot the knee joint about the contralateral compartment (lateral compartment for a *varus* knee). Another technique includes applying a distraction force using a common surgical osteotome by levering the osteotome off the front of the tibia and lifting the femur vertically. Similarly, joint distraction may be performed by placing shim-like spoons or gap sticks between the femur and tibia, or by using laminar spreaders to create the distance between the femur and the tibia.

However, for each of these techniques, the "proper" joint distraction force is subjective, varies from surgeon-to-surgeon, and is difficult for surgeons to learn. In addition, for the first technique described above, applying a *valgus* torque to the tibia for any pose after 30 degrees flexion is extremely difficult because the femur tends to rotate about the femoral head.

Other types of distractors include spring-based, electromechanical, or hydraulic opposing plate spreaders. However, these tend to be large and complex, and due to their size generally require at least some bone to be removed first (provisional resection) to accommodate the device's opposing plates. Yet another device is a force sensing shim. However, like the shim-like spoons or gap sticks, this device generally requires iteratively inserting the device into the joint with various thicknesses until the desired force is achieved, making it time consuming and cumbersome.

SUMMARY

According to one aspect, the present disclosure is directed to a joint distraction lever, having a lever body having a handle portion and a working portion. The lever body includes a fulcrum extending from a bottom surface of the working portion of the lever body and a distal tip, wherein the distal tip is raised above a top surface of the working portion of the lever body. The joint distraction lever is configured to measure a distraction force applied at the distal tip during a distraction procedure when a torque is applied by an external force applied on the handle portion of the lever body. The joint distraction lever further includes an indicator configured to provide feedback related to the distraction force applied at the distal tip, as measured by the joint distraction lever.

According to another aspect, the present disclosure is directed to a method for performing joint distraction that includes moving a joint including a first bone and a second bone into a first flexion position and inserting a joint distraction lever into the space between the first bone and the second bone. The joint distraction lever includes a lever body having a handle portion and a working portion, a fulcrum extending from a bottom surface of the working portion of the lever body, and a distal tip, wherein the distal tip is raised above a top surface of the working portion of the lever body. The joint distraction lever further includes a force measurement device configured to measure a distraction force applied at the distal tip during a distraction procedure when a torque is applied by an external force applied on the handle portion of the lever body. The joint distraction lever further includes an indicator configured to demonstrate the distraction force applied at the distal tip, as measured by the joint distraction lever. The method further includes applying a force to the handle portion of the lever body of the joint distraction lever to cause a torque on the joint distraction lever and receiving feedback from the indicator related to the amount of distraction force being applied to the first bone at the distal tip.

According to another aspect, the present disclosure is directed to an instrumented osteotome including a lever body having a handle portion and a working portion. A fulcrum extends from a bottom surface of the working portion of the lever body and a distal tip is raised above a top surface of the working portion of the lever body. The osteotome further includes a strain gauge for measuring a stress on the lever body to determine a distraction force applied at the distal tip, and a power source for providing voltage to the strain gauge. The osteotome also includes a display electrically coupled to the output of the strain gauge and configured to provide feedback related to the distraction force applied at the distal tip, as measured by the strain gauge. The display is further configured to be in a first state when a first distraction force is applied and to be in a second state when a second distraction force is applied.

The invention is capable of other embodiments and of being practiced or being carried out in various ways. Alternative exemplary embodiments relate to other features and combinations of features as may be generally recited in the claims.

BRIEF DESCRIPTION OF THE FIGURES

The invention will become more fully understood from the following detailed description, taken in conjunction with the accompanying drawings, wherein like reference numerals refer to like elements, in which:

FIG. 1 is a top side view of a joint distraction lever according to a first exemplary embodiment.

FIG. 2A is a lateral side view of the joint distraction lever of FIG. 1.

FIG. 2B is a lateral side view of a joint distraction lever according to another exemplary embodiment.

FIG. 2C is a second lateral side view of the joint distraction lever of FIG. 2B.

FIG. 3A is a bottom side view of the joint distraction lever of FIG. 1.

FIG. 3B is a bottom side view of a joint distraction lever according to another exemplary embodiment.

FIG. 3C is a bottom side view of the joint distraction lever of FIG. 2B.

DETAILED DESCRIPTION

Figure 4:
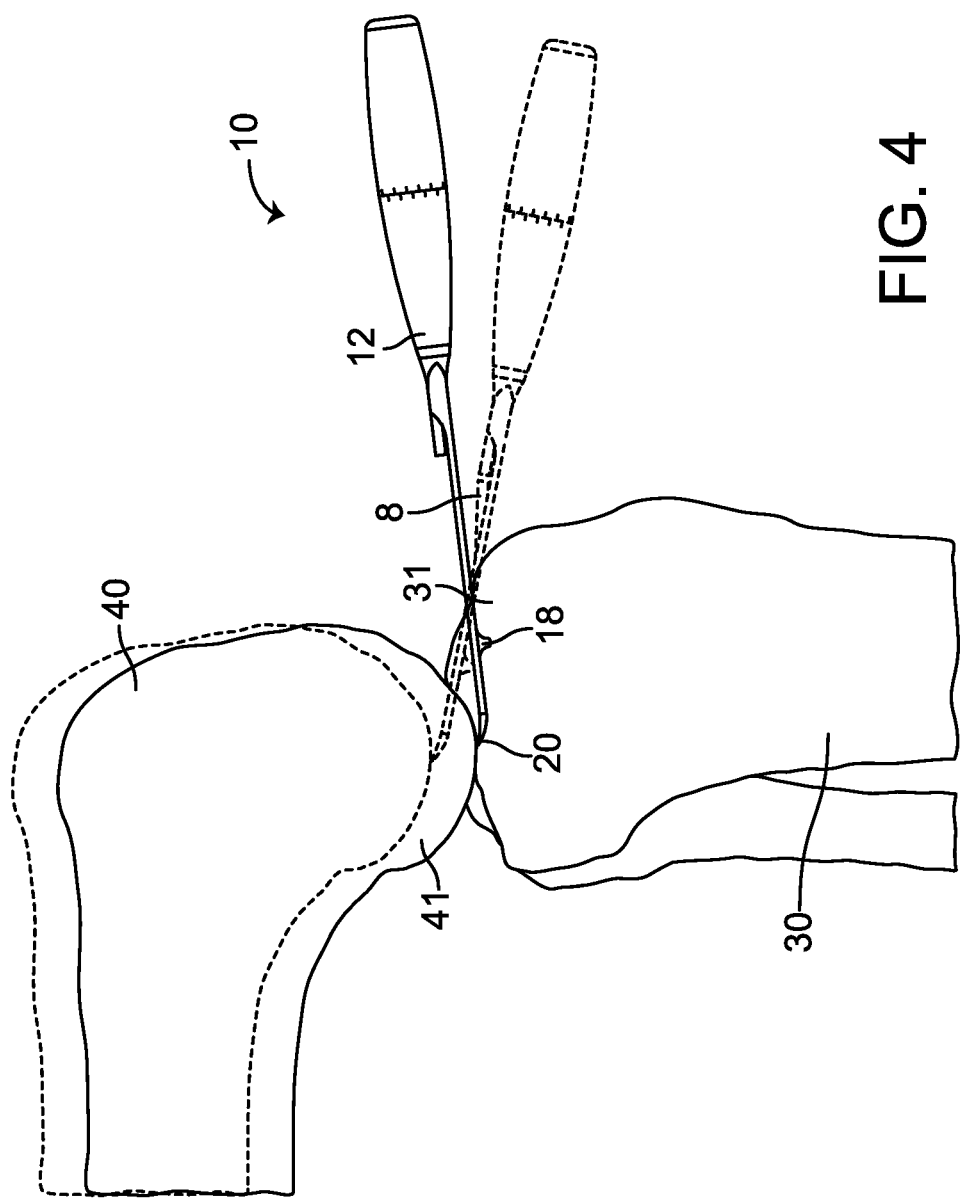
FIG. 4 depicts joint distraction of a patient's knee joint using the joint distraction lever of FIG. 1.
Figure 5:
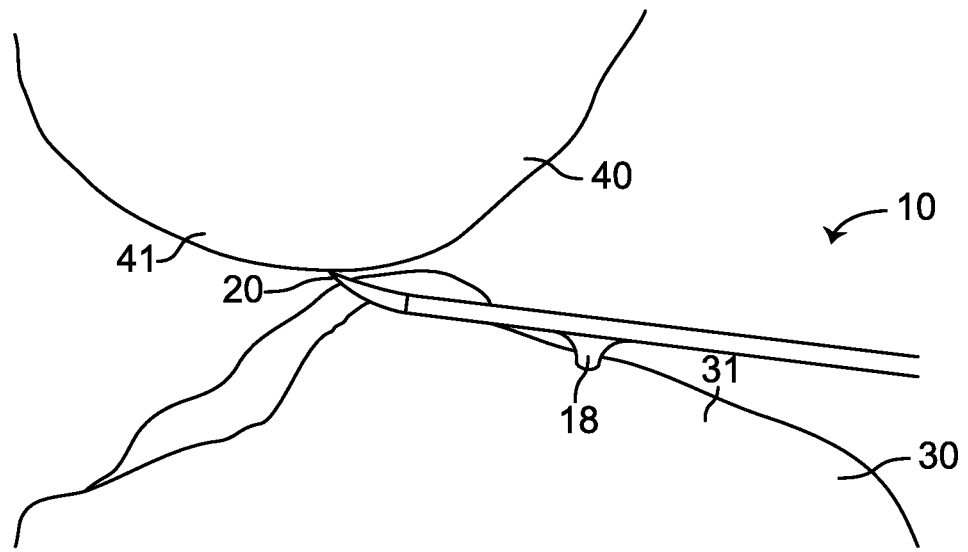
FIG. 5 depicts a closer view of joint distraction of a patient's knee joint using the joint distraction lever of FIG. 1.
Figure 6:
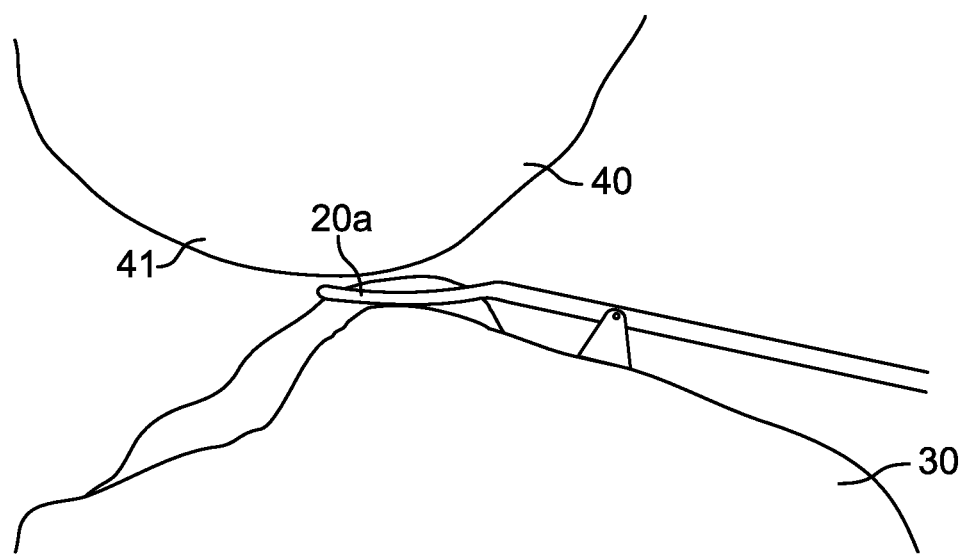
FIG. 6 depicts joint distraction of a patient's knee joint using a joint distraction lever according to another exemplary embodiment.

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Referring to FIGS. 1-3, a joint distraction lever is shown. In certain embodiments, the joint distraction lever is an osteotome 10. Though the present description will refer to the joint distraction lever as the osteotome 10, it is to be understood that the features disclosed herein may be used with and provided in a variety of lever-type devices, which are considered to be within the scope of the present disclosure. As shown in FIGS. 1-3, the various embodiments of osteotome 10 include a lever body 12 having a handle portion 14 and a working portion 16. A fulcrum 18 extends from a bottom face 12b of the working portion 16 of the lever body 12. At a distal end of lever body 12 there is provided a distal tip 20. Distal tip 20 is raised to extend above the top face 12a of the lever body 12. In the embodiments shown, the distal tip 20 curves upwardly from the working portion 16 at the distal end of the lever body 12.

The osteotome 10 preferably has a thin, narrow lever body 12 sized to be inserted into a pre-resection narrow joint space. The lever body 12 may be between 1-3 mm thick at the working portion 16, and in a preferred embodiment is no more than 2 mm thick. In some preferred embodiments, the thickness of the working portion 16 tapers towards the distal tip 20 to no more than 1 mm thick at the tip 20. The width of the working portion 16 may be between 10-22 mm wide to accommodate compartments of various sizes, and in a preferred embodiment is approximately 15 mm wide.

Referring to FIG. 4, it is shown that the fulcrum 18 is configured to rest on a first bone of a joint. The embodiments of the joint distraction device are depicted and described herein as being used in a knee joint, though it should be understood that the joint distraction device may be used in any joint that is suitable for a joint distraction procedure. Thus, in the figure, the fulcrum is shown resting on a tibial plateau 31 of a patient's tibia 30. This provides the support for the osteotome 10 and the point around which the torque is applied and the distraction force will be provided to the distal end of the patient's femur 40 through distal tip 20. As depicted in FIG. 4, as an external force is exerted on the handle portion 14 of the lever body 12, a torque is applied to the lever body 12 about the fulcrum 18. A resulting force is then applied at the distal tip 20 which causes the distraction of the joint, that is, for example, the separation of the first bone (tibia 30) from the second bone (femur 40).

The joint distraction device according to various embodiments is dependent on the force being applied at two known locations: the fulcrum 18 and the distal tip 20. To ensure that forces are being applied only at these two locations, the fulcrum 18 and the tip 20 project from the bottom face 12b and the top face 12a, respectively, of lever body 12 such that the lever body 12 does not inadvertently contact either bone of the joint.

As such, the fulcrum 18 is designed to project from the bottom face 12b to a distance sufficient to prevent contact of the bottom face 12b with the tibia 30 during use. In a preferred embodiment, the fulcrum 18 extends proud of the lever body 12 by at least 2 mm, but may be anywhere between 1-3 mm proud of the lever body 12, or more. In certain embodiments, the widest portion of the fulcrum 18 is between 4-8 mm, and the thickest portion is between 1-2 mm. The fulcrum may be instrumented such that the fulcrum itself is configured to measure the load being applied at the fulcrum. In such an embodiment, an instrumented fulcrum can be attached to a standard osteotome to achieve certain features of the disclosed embodiments without further modification to force measuring aspects of the osteotome. As shown in the embodiment of FIGS. 2A and 3A, the fulcrum 18a shape may be somewhat tapered or sharp into a pointed tip to allow slight penetration into bone and/or cartilage to provide stability of the osteotome 10 during distraction and while the joint poses are being captured.

In the embodiment shown in FIGS. 2B, 2C, and 3C, the fulcrum is a triangular pad 18c. The triangular pad 18c may be connected to the lever body at a rotatable pivot joint. The triangular pad 18c provides greater surface in contact with the bone to minimize penetration into the bone when such penetration would be detrimental or undesirable. Though the pad shown in FIGS. 2B, 2C, and 3C is triangular, other configurations having a narrow top portion to form a portion of a pivot joint, and a wider bottom portion to contact the bone can be used to provide a pivot pad for pivoting of the lever body about the fulcrum. In other embodiments, such as that shown in FIG. 3B, the fulcrum is a linear fulcrum 18b extending laterally across the lever body 12. This embodiment also provides a greater surface area in contact with the bone and may also reduce the penetration of the fulcrum into the bone during use.

The distraction force, and thus the measurement of the distraction force applied through the distal tip 20 (to be discussed in detail below), is sensitive to fulcrum 18 to lift point (tip 20) distance. When the distance from the fulcrum 18 to the raised tip 20 is known or selected, which it will be when the joint distraction lever is used, the applied distraction force can be calculated. The fulcrum 18 to tip 20 distance may be fixed or may be variable and/or adjustable. In a fixed fulcrum to tip embodiment, the spacing may be between 10-25 mm. An adjustable distance embodiment may allow for a greater range of the fulcrum to tip distance. FIG. 3C depicts an embodiment wherein the fulcrum 18 to tip 20 distance can be adjusted by moving the pivot joint along slot 19 and securing it at a desired distance from tip 20. In certain preferred embodiments, the distance between the fulcrum 18 and the tip 20 is fixed at 20 mm. This distance is particularly useful for distraction of the knee joint, as it allows the fulcrum 18 to rest on the anterior plateau 31 of the tibia 30 and the tip 20 to be directly below the femoral condyle 41.

Referring to FIGS. 2 and 4-7, it is shown that the distal tip 20 projects above the top face 12a of the lever body 12. In the embodiments shown, the distal tip 20 of the working portion 16 curves upward to form distal tip 20. Again, in order that forces are applied to the bones of the joint only at the fulcrum 18 and distal tip 20, the distal tip 20 is configured such that the top face 12a of the lever body 12 does not contact the femur 40 during distraction of the joint. The raised tip 20 may stand 1-5 mm proud of the top face 12a of the lever body 12, and in a preferred embodiment is curved to be 4 mm proud of the lever body 12. As shown in the embodiment of FIGS. 2, 4, 5, and 7, the lever body 12 may taper towards the distal tip 20, such that distal tip 20 is pointed. The pointed tip, in a preferred embodiment, has a width of about 1 mm.

The profile of the lever body 12, particularly the distal tip 20, may take on various profiles, not limited to the pointed distal tip shown in the previous embodiments. In one exemplary configuration, such as that shown in FIG. 6, the distal tip 20 takes on the shape of a plate 20a. The shape may be slightly curved to fit with the outer surface of the bone. In some embodiments, the plate 20a at the distal tip is specifically configured for a particular bone or the anatomy of a particular patient. This configuration provides greater contact surface area for torque transmission efficiency as well as to reduce penetration of the bone being distracted. Other configurations of the distal tip may also be used in accordance with additional embodiments of the present invention.

The joint distraction lever may have a rotatable handle portion 14. The rotatable handle portion 14 may allow for a reduction in the amount of torque working laterally during joint distraction. For example, when distracting the knee joint, it is intended to provide the distraction force substantially parallel with the mechanical axis of the joint. However, the surgeon may not be able to achieve exact access and grip on the tool such that all forces are being applied in this direction. Some torque, instead, may be applied sideways on the joint while also being applied in parallel with the mechanical axis. The rotatable handle portion 14 may counteract some of the sideways torque applied by cooperating with the twisting that may occur on the handle when the force is applied at the handle portion 14.

The joint distraction lever, such as osteotome 10, is configured to measure and provide output related to the distraction force applied to the bone of the joint, such as the distal femur 40, by the distal tip 20 during a distraction procedure. The distraction force is measured by a force measurement device. The embodiment of FIG. 1 shows a mechanical force measurement osteotome. In this embodiment, the lever body 12 includes a cut out portion forming a cantilever beam 8. Upon application of an applied force, the cantilever beam 8 tilts upward (as depicted in FIGS. 2C and 4). The cantilever beam 8 may be used to determine the applied force based on its relationship with a reference feature. For example, as shown in FIGS. 2C and 4, the cantilever beam 8 may move towards alignment with tab 9 extending from the handle portion 14. The joint distraction lever can be configured such that alignment of the cantilever beam is with the tab 9 indicates a predetermined force value.

Another non-electronic configuration for determining the distraction force applied at the distal tip 20 is an analog torque wrench that is configured to apply a set specific torque to the wrench body or, particularly, lever body 12. Analog graduations of torque settings may be available, and once determined and set, the lever body 12 will be configured to apply a torque and thus cause a distraction force at the distal tip 20 until a predetermined, desired force is applied. When the preset torque has been met, the wrench, or lever, is configured to indicate that the preset torque has been reached, or otherwise prevent further torque from being applied through the lever body.

In another exemplary embodiment, the force measurement device is a strain gauge. One or more strain gauges may be coupled with the lever body 12 and configured to receive an input voltage provided by a power source. In certain embodiments, the power source is a battery. The battery may be disposable, rechargeable, or take the form of a chargeable capacitor. As the electrical conductor of the strain gauge deforms, as the joint distraction lever deforms as the torque is applied to distract the bones of the joint, the electrical resistance of the electrical conductor of the strain gauge changes. Thus, from the measured electrical resistance of the strain gauge(s), computed using the known or measured input voltage and measured output voltage, the amount of applied stress to the joint distraction lever can be measured and the distraction force computed. A plurality of strain gauges may be arranged and included in the joint distraction lever to form a load cell. The output of the load cell transducer can then be used to convert the force or stress determined by the strain gauges into an electrical signal.

Other mechanisms or tools for measuring the distraction force applied by the joint distraction lever at the distal tip 20 include piezoelectric pressure sensors wherein a charge is generated when a piezoelectric crystal, or other suitable material, of the pressure sensor is stressed. The charge output, or the charge output converted to a voltage signal, for example, may be used to compute and indicate the distraction force being applied by the distraction lever. Similarly, stress to the lever body 12 to compute the distraction force applied at the distal tip 20 can be determined using optical sensors in a cantilever beam configuration. The optical sensors may include an array of optical fibers capable of providing computation of stress and strain by way of wavelength variations between the light source and a detector caused by modifications in the optical fiber body. Finally, a magnetic contact switch may be used to indicate the presence of a load being applied, or can be configured to indicate how much load is being applied.

Figure 7A:
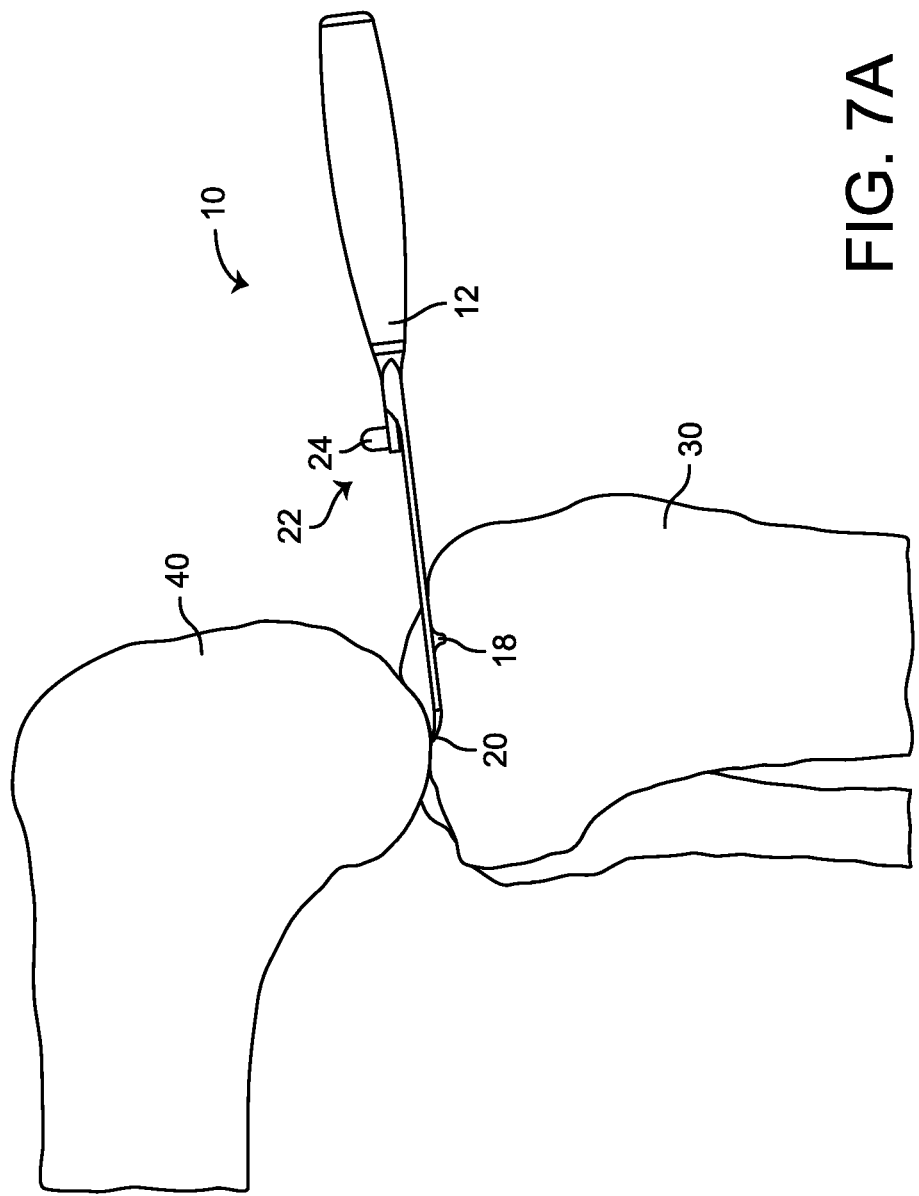
FIGS. 7A-7C depict joint distraction of a patient's knee joint using a joint distraction lever having an indicator according to an exemplary embodiment.
Figure 7B:
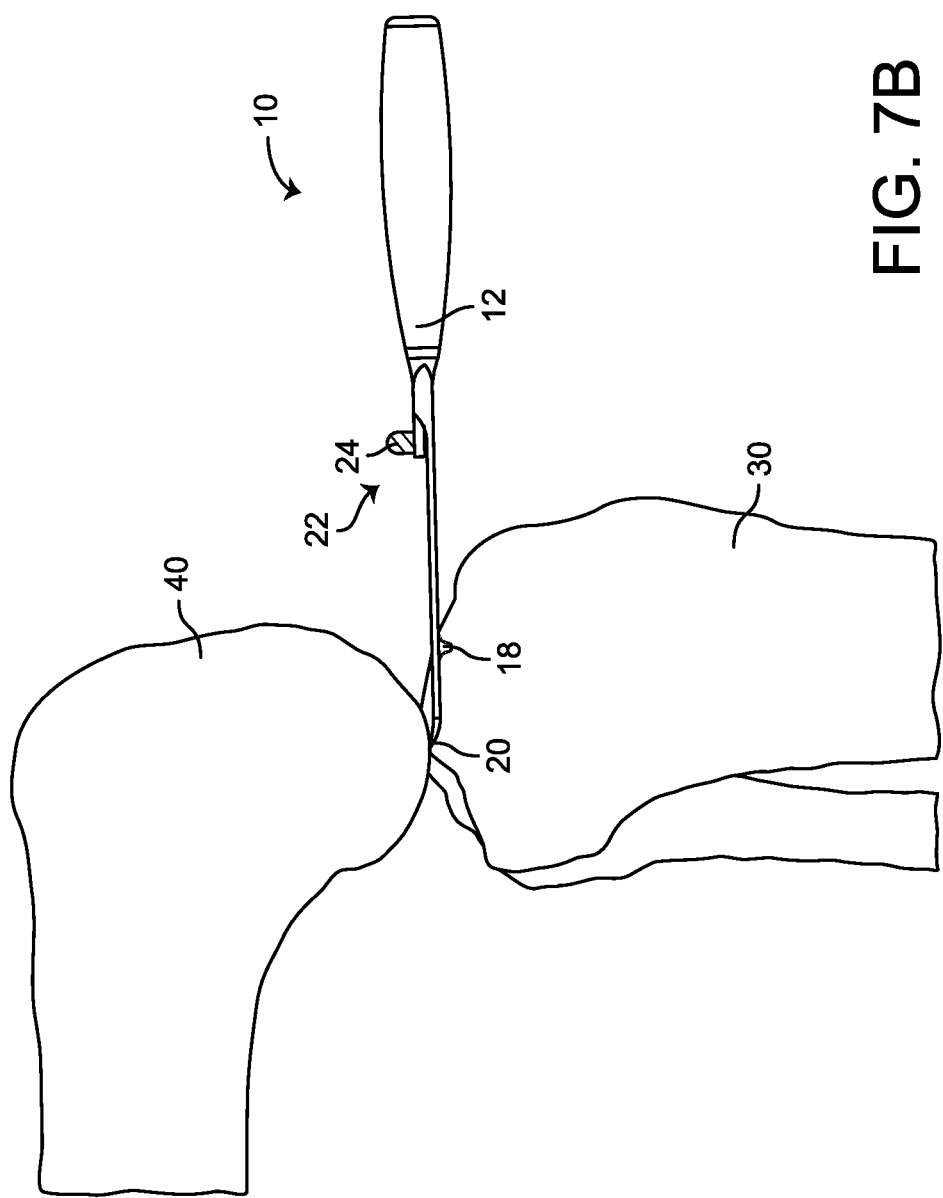
Figure 7C:
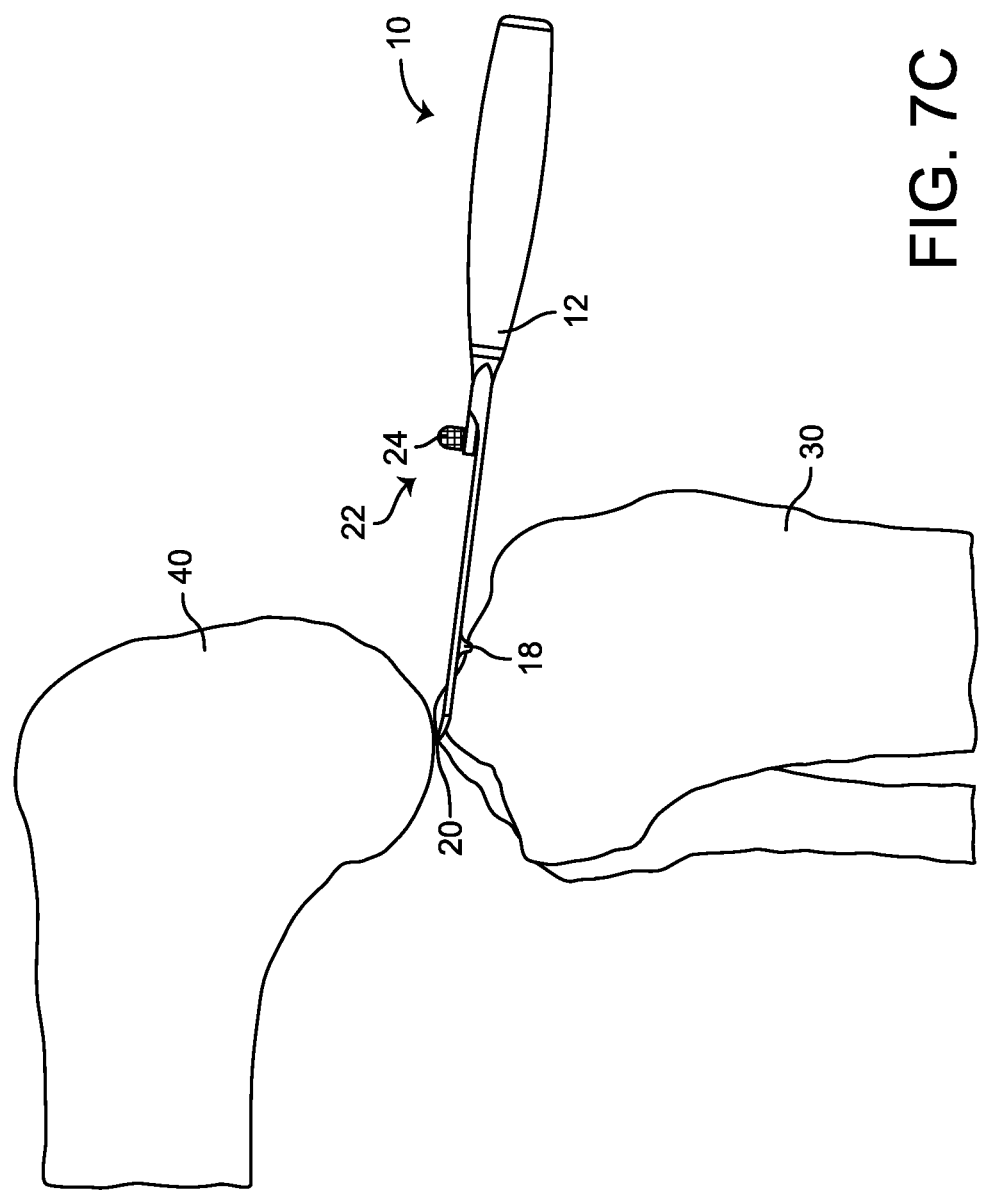

Referring to FIGS. 7A-7C, osteotome 10 includes an indicator 22. The indicator 22 provides feedback to a user related to the distraction force being applied to a first bone of the joint, such as the distal femur, at the distal tip 20. The feedback may indicate the current value of the force being applied, or it may be representative of a particular range of force values, i.e. provide feedback when a predetermined force value has been reached or exceeded. The feedback provided via indicator 22 allows for consistent, repeatable, trainable force application. Distinct from prior methods and systems for joint distraction where force is subjective, changes between surgeons, and is difficult to learn, the joint distraction lever according to the disclosed embodiments provides feedback to the user such that consistent force can be quantified and applied uniformly among different surgeons, between one distraction procedure and the next, and can be applied at any flexion angle. In certain embodiments, the osteotome 10 is configured to apply a force of 85 N+/−15 N. Accordingly, the indicator 22 is configured to provide feedback to the user when the distraction force achieves some predetermined relationship with the desired force value.

FIGS. 7A-7C depict osteotome 10 having an indicator 22 according to a preferred embodiment, wherein the indicator 22 is a light-emitting diode (LED) 24. As shown in FIG. 7A, the LED 24 is in a first illumination state as a first range of distraction force is being applied. For example, as the osteotome 10 is first inserted in the joint space and no force is being applied, or only a low amount of force is being applied, the LED 24 may emit light of a certain color, or remain off. FIG. 7B depicts the LED 24 in a second state once the distraction force has achieved or passed a certain predetermined value. For example, the second illumination state may cause the LED to emit light of a second color. In an exemplary embodiment, the second state may occur when the distraction force reaches 70 N+/−5 N. Finally, FIG. 7C depicts the LED 24 in a third illumination state, indicating to the user the a predetermined, desired distraction force, or a maximum distraction force, has been achieved. For example, the LED may emit light of a third color once the predetermined force has been reached. In an exemplary embodiment, the third state may occur when the distraction force reaches 100 N+/−5 N. Alternatively, the LED may provide other illumination states such as a slow or rapid flashing state to provide an indication that a predetermined force has been reached.

Some embodiments may use a plurality of LEDs. For example, when any force is applied, a first LED may illuminate. Additional LEDs may illuminate successively as the force increases, each illuminating once the force meets a predetermined value. The desired distraction force may be indicated when all of the LEDs on the lever are illuminated.

Similarly, instead of an LED 24, the indicator 22 may provide feedback in the form of a sound emitted from the osteotome, such as a beep or click, or arrangement thereof indicating, for example, a first, second, and third state. Alternatively, the osteotome 10 may provide a single beep, click, or other sound only when the desired, predetermined force value has been reached. Likewise, the indicator 22 may provide feedback in the form of haptic vibration of the joint distraction lever. As with the LED 24 and the sound indicator, the haptic vibration may indicate to a user various of ranges of distraction force being achieved, or provide feedback only at the desired, predetermined distraction force value.

In the mechanical embodiment of FIG. 1, the indicator is the movement of the cantilever beam 8 above the top face 12a of the working portion 16, relative to the height of the reference tab 9 extending from the handle portion 14. In an embodiment wherein the force computation occurs by an analog torque wrench, the indicator 22 is the analog graduations provided. In electronic embodiments, the output of the various strain sensors may be converted into a signal to display a digital representation of the force value on a display window on the lever body 12 itself or on a display or indicator device coupled thereto. The device may further be configured to communicate the computed force wirelessly with an external system which may display the force value on a display device or provide the sound feedback or other indicator to the user of the forces being applied by the joint distraction lever.

In some embodiments, the joint distraction lever may have a preset target distraction force value, and/or preset force values representing the various force stages. In such embodiments, the various indicators indicate when the preset value is reached. In other embodiments, the joint distraction lever may be adjustable. In this way, the surgeon may set the output, i.e., the feedback provided by the indicator, for a selected amount of force. In one example, the surgeon may use the joint distraction lever to first distract the joint. When the surgeon is applying the necessary and desired amount of force to cause distraction of the joint, he or she can set that as the force value that generates a certain output, for example, the force that causes the LED to illuminate. In this way, the same load can be applied consistently and repeatedly by applying a force until that output is again observed. In one exemplary embodiment, shown in FIG. 4, a dial with value hashtags can be adjusted to set the force value and output according to the surgeon's desired load. In other embodiments, an adjustment of the desired or predetermined values can be adjusted via software implemented in the joint distraction lever and/or with the surgical system 900 (described below). Also, referring to FIG. 3C described above, the distance between the fulcrum and tip can be adjusted such that the doctor can adjust the distraction force without adjusting his or her applied force.

Figure 8:
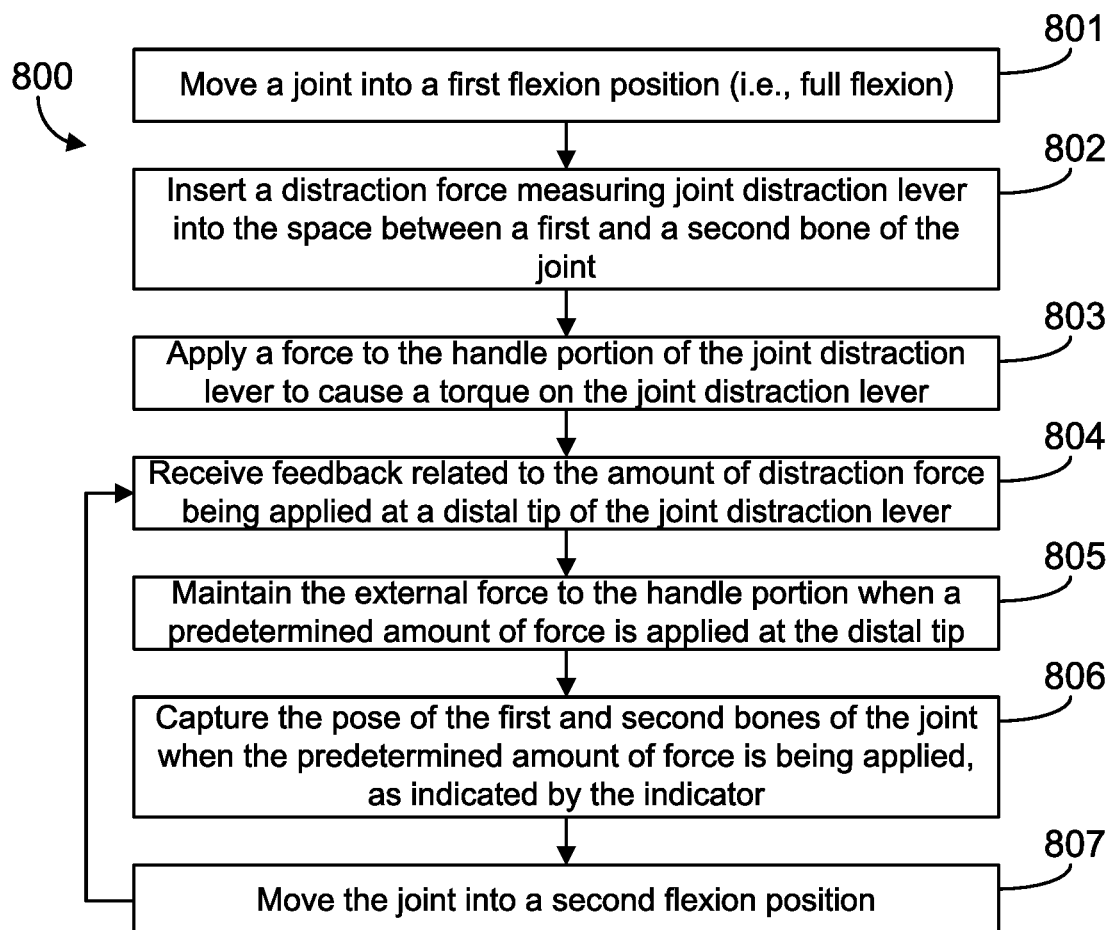
FIG. 8 illustrates one embodiment of a method for performing joint distraction using a joint distraction lever according to an exemplary embodiment.

Referring to FIG. 8, a method 800 for performing joint distraction using a joint distraction lever according to the preferred embodiments is depicted. In step 801, a joint, such as the knee joint including the tibia and the femur, is moved into a first flexion position. In a preferred method, the first flexion position is full flexion though any range of flexion may be used. In step 802, a joint distraction lever according to the exemplary embodiments disclosed herein is inserted into the space between the first and second bones of the joint. An external force may then be applied to the handle portion 14 of the lever body 12 to cause a torque on the joint distraction lever (step 803). In step 804, the user receives feedback related to the amount of distraction force being applied to the first or the second bone of the joint at the distal tip 20 of the joint distraction lever, as measured by the joint distraction lever. In step 805, the user, having achieved and having a desired awareness of the distraction force being applied maintains the force to the handle portion 14 to complete the joint distraction procedure.

Optionally, after step 805, a pose of the first and second bones of the joint is captured when the predetermined distraction force is applied and maintained at the distal tip (step 806). Capturing the pose of the first and second bones in the distracted joint assists with surgical planning to ultimately attain the desired, properly aligned joint post-resection and post-prosthetic implantation. To provide for capturing the pose of the joint, it is contemplated that the exemplary joint distraction lever may be used in conjunction with anatomy navigation systems and methods, which may further be used with a surgical system, such as that depicted in FIG. 9. The figure shows an embodiment of a surgical system 900 that includes a computing system 920, a surgical tool, such haptic device 930, and a tracking system 940. In operation, the surgical system 900 enables comprehensive surgical planning which may include performing distraction of a joint using the osteotome 10 described herein.

Determining the pose of the first and second bones in step 806 may make use of tracking system 940. The tracking (or localizing) system 940 of the surgical system 900 is configured to determine a pose (i.e., position and orientation) of one or more objects during a surgical procedure to detect movement and capture poses of the object(s). For example, the tracking system 940 may include a detection device 941 that obtains a pose of an object with respect to a coordinate frame of reference of the detection device. As the object moves in the coordinate frame of reference, the detection device tracks the pose of the object to detect (or enable the surgical system 900 to determine) movement of the object. Tracked objects may include, for example, tools/instruments, patient anatomy, implants/prosthetic devices, and components of the surgical system 900. Using pose data from the tracking system 940, the surgical system 900 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the computer 921. For example, utilizing pose data from the tracking system 940, the surgical system 900 is able to associate the physical anatomy with a representation of the anatomy (such as an image displayed on the display device 945). Based on tracked object and registration data, the surgical system 900 may determine, for example, (a) a spatial relationship between the image of the anatomy and the relevant anatomy. Additionally, by tracking the relevant anatomy, the surgical system 900 can compensate for and ascertain movement of the relevant anatomy during the surgical procedure, as needed for capturing the pose of the distracted joint at the flexion position.

Registration may include any known registration technique, such as, for example, image-to-image registration (e.g., monomodal registration where images of the same type or modality, such as fluoroscopic images or MR images, are registered and/or multimodal registration where images of different types or modalities, such as MM and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MRI images to an intraoperative scene).

The tracking system 940 may also be used to track the anatomy and the joint distraction lever, or osteotome 10, while applying the distraction force. By tracking the pose (position and orientation) and the movement of the osteotome 10 and the anatomy, the computing system 920 can determine the directional components of the force being produced. As described above, in addition to the forces acting along the mechanical axis, the distraction force may also act in a lateral direction or other direction off-axis from the mechanical axis. Tracking of the objects and determination of the directional components can allow for a determination of the amount of force that is off of the intended axis. This can help the surgeon, or the system automatically, to adjust the application of force for more efficient load transmission, and/or to reduce any injury or damage that may occur may applying distraction forces in directions that are off of the intended axis.

The tracking system 940 may be any tracking system that enables the surgical system 900 to continually determine (or track) a pose of the relevant anatomy of the patient and a pose of the tool 935 (and/or the haptic device 830). For example, the tracking system 940 may comprise a non-mechanical tracking system, a mechanical tracking system, or any combination of non-mechanical and mechanical tracking systems suitable for use in a surgical environment. The non-mechanical tracking system may include an optical (or visual), magnetic, radio, or acoustic tracking system. Such systems typically include a detection device adapted to locate in predefined coordinate space specially recognizable trackable elements (or trackers) that are detectable by the detection device and that are either configured to be attached to the object to be tracked or are an inherent part of the object to be tracked. For example, a trackable element may include an array of markers having a unique geometric arrangement and a known geometric relationship to the tracked object when the trackable element is attached to the tracked object, such as the femur 40 and tibia 30 of a patient. The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

Figure 9:
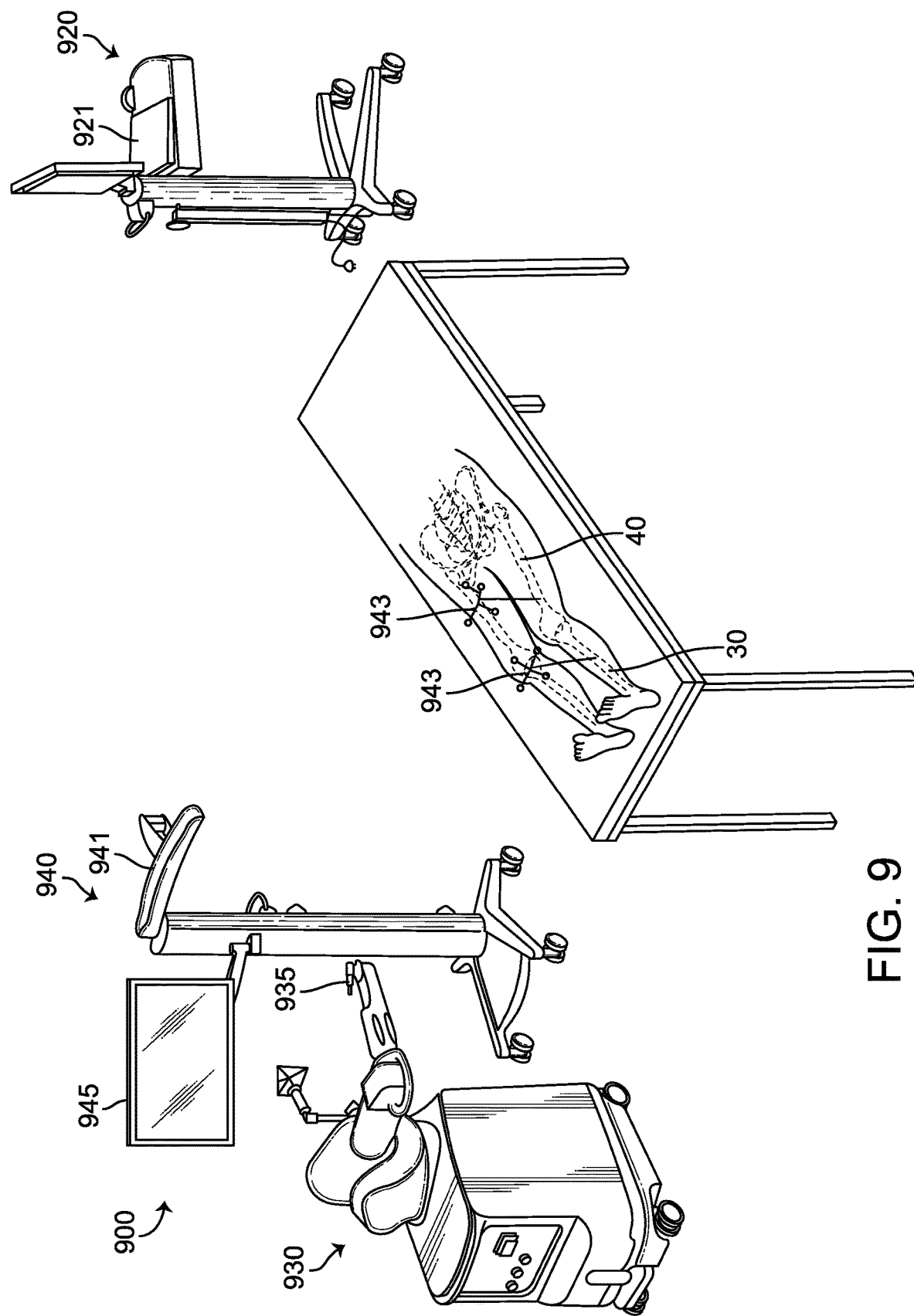
FIG. 9 illustrates a surgical system with which a joint distraction lever according to an exemplary embodiment may be used.

In one embodiment, as shown in FIG. 9, the tracking system 940 includes a non-mechanical tracking system. In this embodiment, the non-mechanical tracking system is an optical tracking system that includes a detection device 941 and at least one trackable element (or tracker), such as anatomy tracker 943, configured to be disposed on (or incorporated into) a tracked object and detected by the detection device 941. The tracker is configured to be affixed to the tracked object in a secure and stable manner and includes an array of markers having a known geometric relationship to the tracked object. The markers may be active (e.g., light emitting diodes or LEDs) or passive (e.g., reflective spheres, a checkerboard pattern, etc.) and preferably have a unique geometry (e.g., a unique geometric arrangement of the markers) or, in the case of active, wired markers, a unique firing pattern. In operation, the detection device 941 detects positions of the markers, and the unique geometry (or firing pattern) and known geometric relationship to the tracked object enable the surgical system 900 to calculate a pose of the tracked object based on the positions of the markers.

As stated above, a virtual representation of the anatomy, such as the knee joint, can be displayed on display device 945. The display device 945 may also display the distraction force measurement obtained by the force measurement lever. The osteotome 10 may communicate wirelessly or via a coupled connection with the surgical system 900, or other computing or display system, to provide the distraction force measurement for display on an external device, such as the display device 945.

Computing system 920 may be configured to acquire and use the data obtained during a joint distraction procedure to complete a surgical planning procedure. Thus, computing system 920 may capture and store the pose of the first and second bones of the joint via information provided by tracking system 940. The captured pose of the joint may be used to plan bone resection and prosthetic implant placement for proper joint balance and alignment. The computing system 920 of surgical system 900 may be further configured to define a surgical plan based on the captured pose(s) of the distracted joint. The computing system 920 then allows surgical system 900 to implement the surgical plan using the tracking system 940 to, for example, track the pose of a surgical tool relative to the patient's anatomy, and may also provide haptic feedback through haptic device 930 having surgical tool 935 based on a haptic boundary created during surgical planning. Haptic device 930 provides surgical guidance to a surgeon in order to keep the surgical tool 935 from deviating from the surgical plan created based on the joint distraction procedure and other aspects of surgical planning.

U.S. Pat. No. 8,010,180, titled "Haptic Guidance System and Method," granted Aug. 30, 2011, which is hereby incorporated by reference herein in its entirety, describes an exemplary surgical system with which the presently described joint distraction lever may be used during a joint distraction procedure and for bone resection and implant planning.

Referring back to the method depicted in FIG. 8, optionally, after step 806, the joint is moved to a second flexion position (step 807) and to any number of additional flexion positions, and the poses are captured with the predetermined resection force applied to the joint. In these poses, with the distraction force applied, the knee joint is in the desired post-resection final position. After collection of poses, bone resection, implant positioning, and implant characteristics are planned so as to maintain this relative alignment by making the femoral and tibial components contact (or be slightly gapped to allow for some laxity). Once the bone is resected at this desired plan and the trials and/or implants are secured to the bone, the leg will then be in the desired pre-resected posed positions.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

The invention includes methods that may be performed using the subject devices. The methods may include the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

What is claimed is:

1. A surgical system, comprising:
a robot;
a joint distraction lever configured to be inserted into a joint of a patient and to determine a distraction force based on deformation of the joint distraction lever;
a tracking system configured to track poses of a first bone and a second bone of the joint and the joint distraction lever while the joint distraction lever is inserted into the joint and distracting the joint; and
a computing system programmed to:
determine a directional component of the distraction force based on the poses of the joint and the joint distraction lever; and
cause automatic adjustment of application of the distraction force with the joint distraction lever based on the directional component.

2. The surgical system of claim 1, wherein the automatic adjustment reduces an amount of the distraction force which is directed off of an intended axis for the distraction force.

3. The surgical system of claim 1, wherein the direction component points in a direction lateral to a distraction of the joint.

4. A surgical system, comprising:
a robot;
a joint distraction lever configured to be inserted in a joint of a patient, comprising:
 a lever body comprising a working portion;
 a distal tip coupled to the working portion; and
 a fulcrum extending from a bottom surface of the working portion and spaced apart from the distal tip;
 wherein the joint distraction lever is configured to determine a distraction force based on deformation of the joint distraction lever;
a tracking system configured to provide tracking information indicating relative poses of the distraction lever while the joint distraction lever is inserted into the joint and distracting the joint, a first bone of a joint distracted by the distraction lever, and a second bone of the joint distracted by the distraction lever; and
a computing system comprising non-transitory memory and a processor, the non-transitory memory storing programming executable by the processor to perform operations comprising:
determining a directional component of the distraction force; and
causing automatic adjustment of application of the distraction force with the joint distraction lever based on the directional component.

5. The surgical system of claim 4, wherein the fulcrum is configured to be inserted into a space between the first bone and the second bone.

6. The surgical system of claim 5, wherein the distal tip is configured to be inserted into the space between the first bone and the second bone so that the distraction force can be exerted between the distal tip on the first bone and the fulcrum on the second bone.

7. The surgical system of claim 4, the lever body further comprising a handle portion configured to receive an external force to cause a torque on the joint distraction lever.

8. The surgical system of claim 7, wherein, responsive to the torque on the joint distraction lever, the distal tip is configured to push on a first bone and the fulcrum is configured to push on a second bone causing the deformation of the joint distraction lever.

9. The surgical system of claim 4, further comprising an indicator configured to provide feedback demonstrating the distraction force applied at the distal tip.

10. The surgical system of claim 9, wherein the feedback indicates a current value of the distraction force has reached a predetermined value.

11. The surgical system of claim 9, wherein the indicator is configured to provide visual feedback relating to the distraction force.

12. The surgical system of claim 11, wherein the indicator is configured to change from a first state to a second state to indicate a current value of the distraction force has reached a predetermined value.

13. The surgical system of claim 12, wherein the indicator is configured to provide a first indication when the distraction force exceeds a first predetermined value and a second indication when the distraction force exceeds a second predetermined threshold.

14. The surgical system of claim 4, wherein the fulcrum is movable relative to the working portion to vary a distance between the fulcrum and the distal tip.

15. The surgical system of claim 4, the joint distraction lever comprising a force measurement device configured to measure the distraction force, wherein the force measurement device is at least one of a strain gauge, a piezoelectric pressure sensor, a magnetic contact switch, and an optical sensor comprising an array of optical fibers.

16. The surgical system of claim 4, wherein the directional component of the distraction force points along a mechanical axis of the joint.

17. The surgical system of claim 16, wherein the computing system is configured to receive, from the tracking system, the position information while the joint distraction lever is used to distract the joint.

18. The surgical system of claim 17, wherein the directional component of the distraction force points in a direction lateral to a distraction of the joint.

19. The surgical system of claim 4, wherein responsive to an indicator providing feedback indicating a current value of the distraction force has reached a predetermined value, the tracking system is configured to capture a pose of the bone of the joint.

20. The surgical system of claim 19, wherein responsive to moving the first bone of the joint to a second position, the tracking system is configured to capture a second pose of the first bone of the joint in the second position.

* * * * *